United States Patent
Wang et al.

(10) Patent No.: US 7,361,257 B2
(45) Date of Patent: Apr. 22, 2008

(54) ELECTROCHEMICAL SCREENING SYSTEM

(75) Inventors: Youqi Wang, Atherton, CA (US); Martin Devenney, Mountain View, CA (US); Alexander Gorer, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 854 days.

(21) Appl. No.: 10/642,386

(22) Filed: Aug. 15, 2003

(65) Prior Publication Data
US 2005/0035002 A1 Feb. 17, 2005

(51) Int. Cl.
*G01N 27/403* (2006.01)
*G01N 27/333* (2006.01)

(52) U.S. Cl. .................. 204/400; 204/416; 204/434

(58) Field of Classification Search .......... 205/775, 205/789, 789.5, 790, 81, 82, 83; 204/400, 204/416, 434
See application file for complete search history.

(56) References Cited

U.S. PATENT DOCUMENTS

| | | | |
|---|---|---|---|
| 2,841,548 A | | 7/1958 | Perlman |
| 4,166,020 A | * | 8/1979 | Trampert ................ 204/416 |
| 4,172,777 A | * | 10/1979 | Yamamoto et al. ......... 204/406 |
| 4,696,103 A | * | 9/1987 | Behl et al. ................ 29/825 |
| 4,863,572 A | * | 9/1989 | Jasinski ................. 205/775.5 |
| 4,956,067 A | | 9/1990 | Yun et al. ................ 204/212 |
| 5,120,421 A | | 6/1992 | Glass et al. |
| 5,217,112 A | * | 6/1993 | Almon .................. 205/794.5 |
| 5,445,726 A | * | 8/1995 | Cammann ............... 205/780.5 |
| 5,985,356 A | | 11/1999 | Schultz et al. ............... 427/8 |
| 6,045,671 A | | 4/2000 | Wu et al. .............. 204/298.11 |
| 6,106,692 A | * | 8/2000 | Kunimatsu et al. ......... 205/775 |
| 6,187,164 B1 | * | 2/2001 | Warren et al. .............. 205/81 |

(Continued)

FOREIGN PATENT DOCUMENTS

WO   WO 98/14641   4/1998

(Continued)

OTHER PUBLICATIONS

Yabe et al. ("Rotating Ring Disk Electrode in Molten Chloride," Electrochimica Acta, vol. 34, No. 10, pp. 1479-1483, 1989).*

(Continued)

*Primary Examiner*—Alex Noguerola
(74) *Attorney, Agent, or Firm*—Cindy Kaplan

(57) ABSTRACT

Devices and methods for evaluating an electrochemical reaction are disclosed. A device includes an electrochemical cell having a cavity for containing a liquidus electrolyte, a first working electrode having at least one electrolytic surface at least partially within the cavity, and a second counter electrode having at least one electrolytic surface at least partially within the cavity. The first working electrode includes a body and an insert supported by the body. The electrolytic surface of the working electrode is formed on or integral with the insert. The insert and body are each formed from a high-temperature material which allows for preparation or processing of the electrolytic surface at a temperature of at least 300° C. The device further includes a drive system detachably coupled to the first working electrode or a portion thereof for effecting relative motion between the electrolytic surface of the working electrode and a bulk portion of the liquidus electrolyte.

72 Claims, 7 Drawing Sheets

U.S. PATENT DOCUMENTS

| | | | |
|---|---|---|---|
| 6,251,245 B1 * | 6/2001 | Satsutani et al. | 204/416 |
| 6,364,956 B1 | 4/2002 | Wang et al. | 118/726 |
| 6,423,193 B1 | 7/2002 | Miller et al. | |
| 6,455,316 B1 | 9/2002 | Turner et al. | 436/37 |
| 6,468,410 B1 | 10/2002 | Donne | |
| 6,468,806 B1 | 10/2002 | McFarland et al. | 436/518 |
| 6,621,263 B2 * | 9/2003 | Al-Janabi et al. | 324/200 |
| 6,884,333 B2 * | 4/2005 | Landau | 205/81 |

FOREIGN PATENT DOCUMENTS

| | | |
|---|---|---|
| WO | WO 00/17413 | 3/2002 |
| WO | WO 02/48841 | 6/2002 |

OTHER PUBLICATIONS

Strycker et al. ("Development of a platinum rotating disc electrode for dynamic electrochemical measurements in glass melts," Journal of Non-Crystalline solids 289 (2001) 106-112).*

Stojanovic et al. ("Development of a rotating ring-disc electrode for high temperature studies in cryolite-based melts," journal of Applied Electrochemistry 25 91995) 456-461).*

Ito et al. (Rotating Ring Disk Electrode in Molten Chloride Systems, Materials Science Forum vol. 73-75 (1991) pp. 409-414).*

Derwent abstract of Kunimatsu et al. (US 6,106,692). Aug. 22, 2000.*

"Coating" definition from Webster's Third New International Dictionary, unabridged. 1993.*

Chemical Elements.com—Molybdenum downloaded from www.chemicalelements.com on Mar. 20, 2007.*

Chemical Elements.com—Gold downloaded from www.chemicalelements.com on Mar. 20, 2007.*

"Chart of COE's Coefficient of Thermal Expansion" from www.lucasmilpaupt.com on Mar. 21, 2007).*

Ramaswami et al. ("Rotating Disk studies in Molten Carbonates I. Electrode Design," J. Electrochem. Soc., vol. 141, No. 3, Mar. 1994).*

Schmidt et al., "Rotating Disk Electrode Measurements on the CO Tolerance of a High-Surface Area Pt/Vulcan Carbon Fuel Cell Electrocatalyst," Journal of the Electrochemical Society (1999), 146(4), 1296-1304.

Schmidt et al., "Characterization of High-Surface-Area Electrocatalysts Using a Rotating Disk Electrode Configuration" Journal of the Electrochemical Society (1998), 145(7), 2354-2358.

"Rotating Disk Electrode for Voltammetry" Metrohm Ltd, Metrohm Ion Analysis, Dec. 1995.

"BAS RDE-2 Rotating Disk Electrode" wysiwyg://12/http://www.bioanalytical.com/products/ec/rde-2.html, Apr. 15, 2003.

"Electrochemistry Refresher" http://www.bath.ac.uk/-chascf/java/electrochemistry/elec/17html/hydro.htm.

Bard, Allen J. et al., "Electrochemical Methods, Fundamentals and Applications", Chapter 8, pp. 280-312, 1980.

* cited by examiner

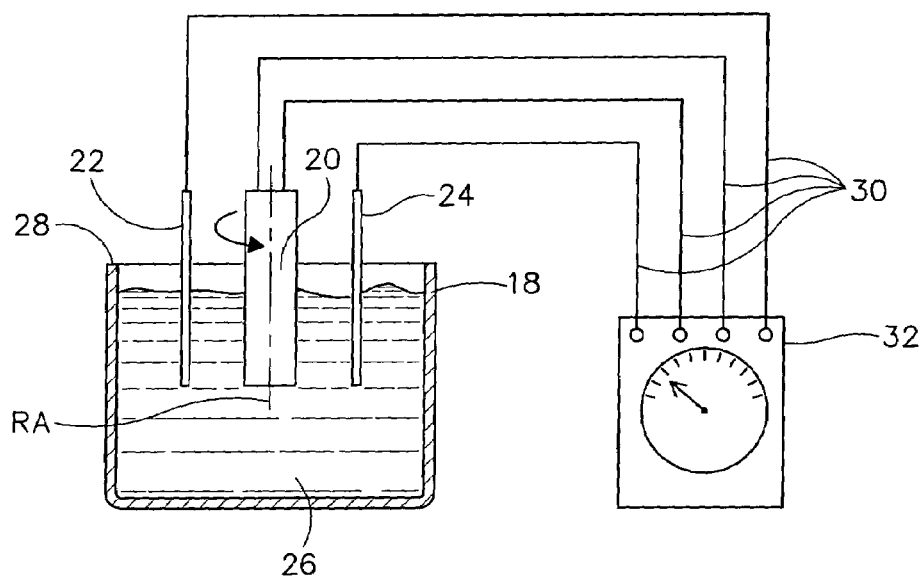
FIG. 1
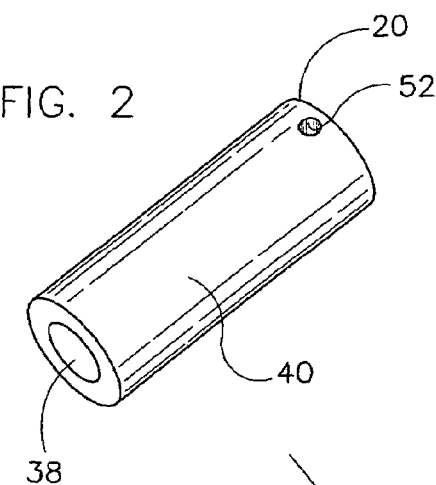
FIG. 2
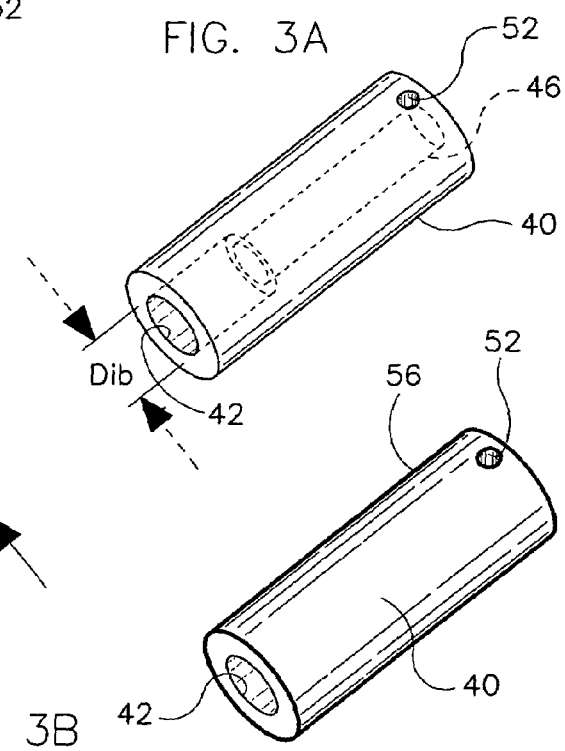
FIG. 3A
FIG. 3B
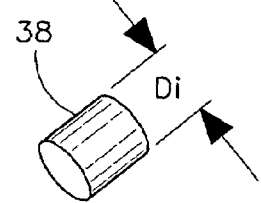
FIG. 4

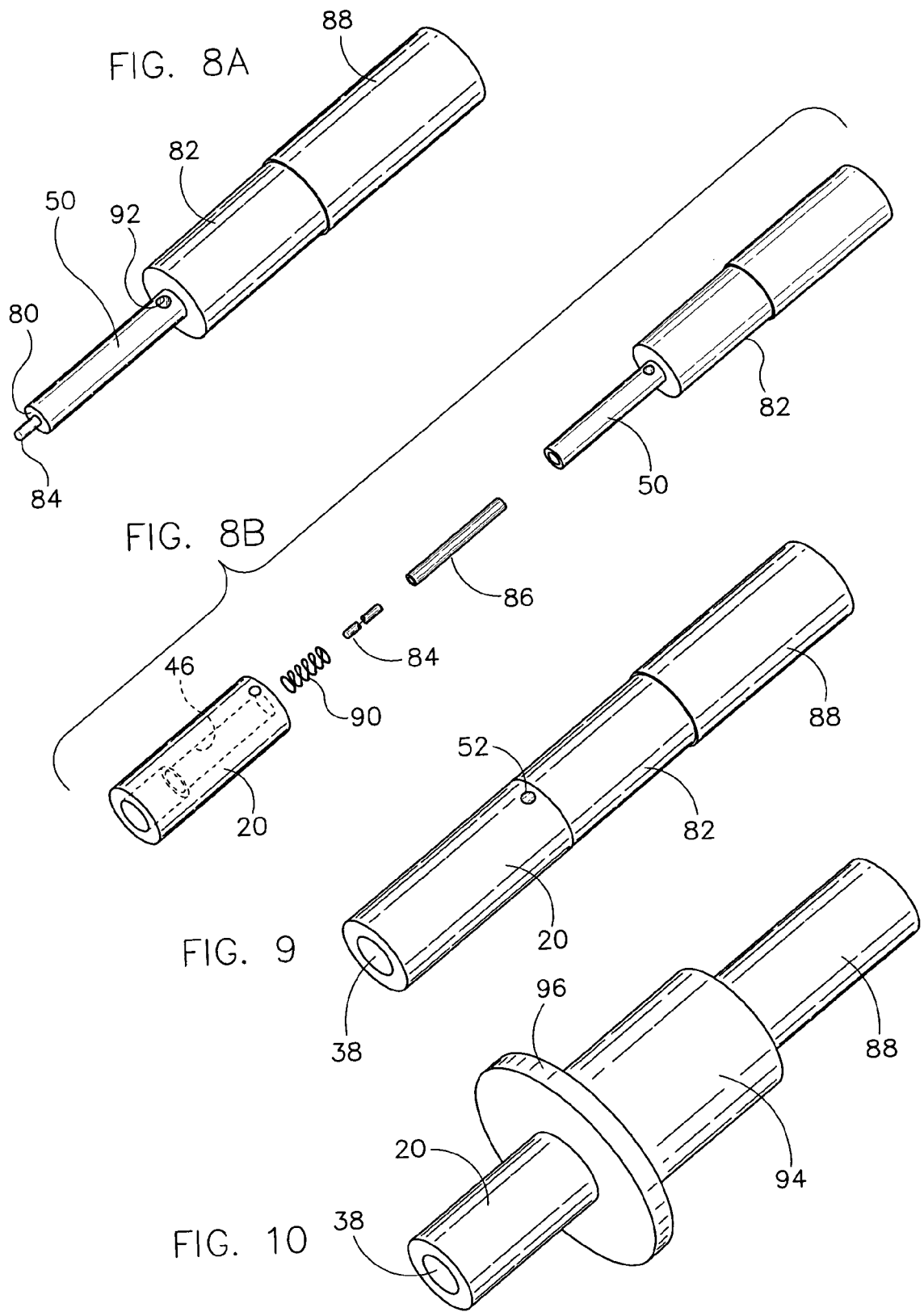

ELECTROCHEMICAL SCREENING SYSTEM

FIELD OF THE INVENTION

The present invention relates generally to electrochemical screening systems, and more specifically, a rotating disk electrode for use in electrochemical screening systems, which can be subjected to high temperature processing conditions or testing environments.

BACKGROUND OF THE INVENTION

A rotating disk electrode (RDE) is one of a number of hydrodynamic voltammetric techniques that is widely used for the study of kinetic and mechanistic electrochemical processes at solid electrodes as well as for electroanalytical applications. RDEs are used in a variety of electrochemical measurement applications, including, for example, battery characterization, measurements of electrocatalyst activity such as for example electrocatalysts for Proton Exchange Membrane Fuel Cells, corrosion studies and electroplating and electrocodeposition studies. The RDE technique is commonly used for the electroanalysis of trace metal components such as mercury and organic additives in plating baths. An electrochemical reaction is a reaction involving the transfer of charge as a part of a chemical reaction. Typical electrochemical reactions in corrosion are metal dissolution and oxygen reduction. The RDE controls the transport regime of electroactive species toward the electrode. Rotating disk electrodes are typically constructed from a disk of electrode material (e.g., gold, glassy carbon, or platinum) imbedded in a rod of insulating material (e.g., Teflon). The electrode is attached to a motor and rotated at a certain speed. The movement of rotation leads to a well-defined laminar liquidus electrolyte flow pattern that can be predicted mathematically. The rotating device acts as a pump, pulling the liquidus electrolyte toward it and then throwing the electrolyte outward.

Conventional rotating disk electrodes are temperature limited, due to their construction materials and structures. For example, conventional RDEs use Teflon or other polymers as electrical insulating or sealing materials, which limit the processing temperature of the RDE to less than 300° C. Furthermore, polymeric materials typically have a thermal expansion coefficient (TEC), which is orders of magnitude larger than typical RDE core materials (e.g., graphite, glassy carbon), resulting in limited temperature ranges for measurement applications.

In preparing rotating disk electrodes for certain applications, it is desired to subject the electrode or electrode materials to high processing temperature (e.g., greater than 300° C.) or to a specific processing environment. It may also be desired to carry out measurements at elevated temperature (e.g., greater than 80° C.). Furthermore, for many applications it is desired that the rotating disk electrodes are detachable from a mechanical shaft which couples the electrode to a drive motor during testing, so that only the RDE is subject to specific processing or treatment at stringent environments. It is further desired to have a RDE structure that allows for a four wire connection near the RDE tip to reduce electrical noise originated from rotational coupling of electric contacts.

SUMMARY OF THE INVENTION

Devices and methods for evaluating an electrochemical reaction are disclosed. A device includes an electrochemical cell having a cavity for containing a liquidus electrolyte, a first working electrode having at least one electrolytic surface at least partially within the cavity, and a second counter electrode having at least one electrolytic surface at least partially within the cavity. The first working electrode includes a body and an insert supported by the body. The electrolytic surface of the working electrode is formed on or integral with the insert. The insert and body are each formed from a high-temperature material which allows for preparation or processing of the electrolytic surface at a temperature of at least 300° C. The device further includes a drive system detachably coupled to the first working electrode or a portion thereof for effecting relative motion between the electrolytic surface of the working electrode and a bulk portion of the liquidus electrolyte.

In another aspect of the invention, an apparatus for simultaneously evaluating multiple electrochemical reactions comprises an electrochemical cell having a cavity for containing a liquidus electrolyte and a plurality of working electrodes each having at least one electrolytic surface positioned at least partially within the cavity. The electrolytic surface is defined by different materials as compared between each of the plurality of working electrodes. The apparatus further includes a plurality of counter electrodes each having at least one electrolytic surface positioned at least partially within the cavity and a drive system coupled to the first working electrodes or a portion thereof for effecting relative motion between the electrolytic surface of the working electrode and a bulk portion of the liquidus electrolyte.

A high temperature rotating disk electrode (RDE) and method of making are also disclosed. The rotating disk electrode includes an insert formed from an electrode material and a tubular member having an opening formed at one end thereof for receiving the insert. A coating may be applied to an external surface of the tubular member to form an electrical insulating sleeve or chemical barrier that is electrochemically inert for intended usage. The material of the body and the material of the insert allow for processing of the rotating disk electrode at temperatures greater than 300° C.

The RDE may further comprise a coating applied by a variety of processes to the exposed end of the insert. The coating may be applied, for example, by physical vapor deposition, electroplating, liquid dispensing of chemical solution, or powder impregnation, aimed at modifying the exposed end face of the insert or forming desired electrode at the surface for various applications.

A method of making the RDE generally comprises providing a cylindrical body and applying an external coating to the cylindrical body to create an external sleeve formed from an electrical insulating or electrochemically inert material. An insert formed from an electrode material is inserted into an opening in one end of the body.

In another aspect of the invention, the RDE comprises an insert formed from an electrode material and a body having a longitudinal opening formed at one end thereof for receiving the insert. The insert and the body opening are sized to create a liquid tight seal therebetween within the desired temperature range under intended measurement environment and the material of the body and the material of the insert allow for processing of the rotating disk electrode at temperatures greater than 300° C.

In another aspect of the invention, a parallel electrochemical apparatus for screening a plurality of materials generally comprises a plurality of electrodes, each of the electrodes having a material applied to the exposed end face of the insert and a plurality of cells. The cells each contain at least one of the plurality of electrodes and are movable independent from one another to vary an insertion depth of the electrodes relative to the depth of liquidus electrolyte contained within the cell.

In yet another aspect of the invention, a method for parallel electrochemical screening of materials generally comprises providing a cell having a reservoir containing a liquidus electrolyte and inserting a plurality of working electrodes into the electrolyte, each of the electrodes having a material applied to one end thereof. The method further includes inserting a plurality of counter electrodes and at least one reference electrode into the electrolyte and performing electrochemical testing to screen materials applied to the plurality of working electrodes.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

FIG. 1 is a schematic illustrating a rotating disk electrode in a cell with a reference electrode and counter electrode.

FIG. 2 is a perspective of the rotating disk electrode of FIG. 1.

FIG. 3A is a perspective of a tubular member of the rotating disk electrode of FIG. 2.

FIG. 3B is a perspective of the tubular member of FIG. 3A with an external sleeve.

FIG. 4 is a perspective of an insert of the rotating disk electrode of FIG. 2.

FIG. 8A is a perspective of a drive shaft configured for coupling the rotating disk electrode to a motor.

FIG. 8B is an exploded view of the drive shaft of FIG. 8A and the rotating disk electrode of FIG. 2.

FIG. 9 is a perspective of the drive shaft connected to the rotating disk electrode of FIG. 2.

FIG. 10 is a perspective of the coupled shaft and rotating disk electrode with a jacket placed over a connection joint.

Corresponding reference characters indicate corresponding parts throughout the several views of the drawings.

DETAILED DESCRIPTION OF THE INVENTION

Figure 5:
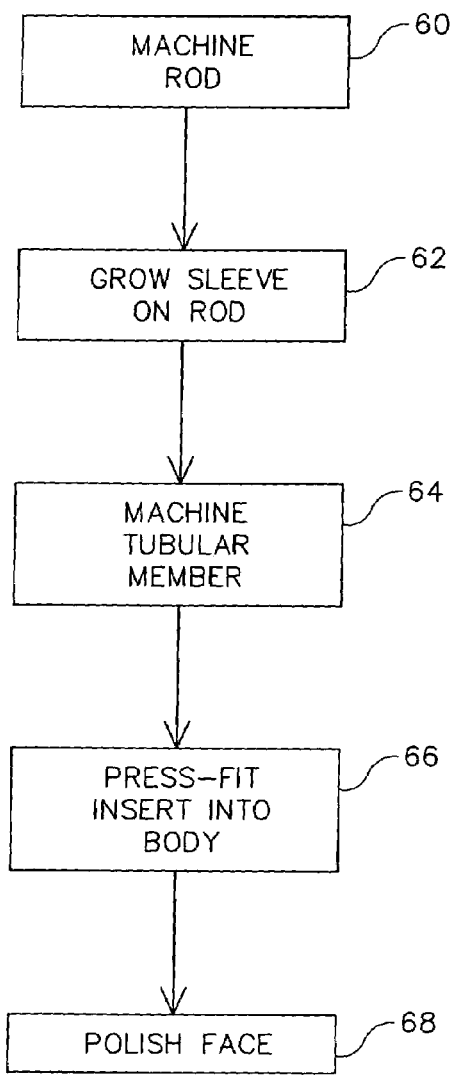
FIG. 5 is a flowchart illustrating a first process for manufacturing the rotating disk electrode of FIG. 2.

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Referring now to the drawings, and first to FIG. 1, an example of an electrochemical cell 18 containing an electrode 20 of the present invention is shown. The electrochemical cell 18 includes a container 28 comprising a cavity containing a bath of liquidus electrolyte 26 and a working electrode (first electrode) 20, a counter electrode (second electrode) 24, and a reference electrode (third electrode) 22, all mounted at least partially within the cavity and exposed to the liquidus electrolyte. Each electrode 20, 22, 24 is attached to at least one connecting wire 30 which is coupled to a measurement instrument 32, such as a commercial potentiostat. An electrical connection to each of the electrodes is provided, for example, by spot-welding, soldering, or bolting the connecting wires 30 to the electrodes 22, 24, or a shaft connecting the electrodes 20 to a motor (not shown). The connecting wires 30 are isolated from the liquidus electrolyte 26.

The term 'liquidus electrolyte' as used herein refers to a solution which conducts electrical current and supports ionized particles. The liquidus electrolyte may be any suitable solution including aqueous or organic electrolytes, molten salt electrolytes as well as ionic liquids. The liquidus electrolyte composition, including aeration and pH, is selected based on the application, as is well known by those skilled in the art.

In one example, the counter electrode 24 supplies the current and the reference electrode 22 measures the electric potential of the working electrode 20. The counter electrode 24 is designed to be inert in the conditions to which it is exposed in order to avoid contamination of the liquidus electrolyte 26. Any suitable material, such as platinum or graphite may be used. In this example, the counter electrode 24 is able to pass sufficient current into the liquidus electrolyte 26 without needing an excessive cell voltage, generating significant heat, having significant chemical reaction which alters the chemical properties of the electrolyte, or causing significant gassing. The liquidus electrolyte temperature is preferably controlled, or at least measured, as the rates of electrochemical reactions are typically temperature dependent. It is to be understood that the cell 18 shown in FIG. 1 and described above is only one example, and working electrode 20 may be used in other types of cells with different configurations, without departing from the scope of the invention.

The working electrode 20 may be used for in-situ synthesis and subsequent processing of metal alloys and other materials. The working electrode 20 is preferably configured to withstand high processing temperature or testing environment so that the electrode may be used in applications which require a high temperature process to be performed. For example, a high temperature process may be used to apply a material (coating) to a portion of the exposed end of the electrode 20 for testing. The working electrode 20 is preferably configured to withstand processing temperatures of greater than 300° C., and in some embodiments may be configured, for example, to withstand temperatures of 600° C., 1000° C., 2000° C., or greater than 2000° C. For example, the electrode 20 may be used in a PVD (physical vapor deposition) or electroplating system which applies a coating to a portion of the electrode 20 or an array of electrodes. The working electrode 20, or at least a portion thereof, is preferably configured to be detachable from an array after synthesis so that the electrode can be used to screen the coatings (e.g., alloys or materials).

The working electrode 20 may also be used in experiments which require high temperature testing in the cell (e.g., greater than 80° C.). In addition to high temperature measurements in aqueous or organic electrolytes, it might be desirable to test in molten salt electrolytes as well as ionic liquids. It is to be understood that these are only examples and that the working electrode 20 may be utilized in many other applications.

In one embodiment, the working electrode 20 is a rotating disk electrode (RDE) and is preferably configured as a high temperature rotating disk electrode (HTRDE). It is to be understood that the working electrode may have shapes and configurations other than shown in FIG. 1 without departing from the scope of the invention. In the following example, a rotating disk electrode is used as the working electrode 20, however, the rotating disk electrode described below is only one example of a working electrode that may be used for synthesis and screening.

FIG. 2 illustrates one embodiment of a working electrode 20 of the present invention. The electrode 20 is in the form of a rotating disk electrode which includes an insert 38 (FIG. 4) formed from an electrode material (i.e., electrically conducting material with desired electrochemical properties) and a body 40 formed from a solid material capable of withstanding high temperatures. The insert 38 is supported by the body and includes an electrolytic surface formed on or integral with the insert. As described below, the insert 38 may be formed from a number of materials, including, for example, graphite, glassy carbon, gold, or platinum. The body 40 may be formed, for example, from aluminum, stainless steel, alumina, quartz, sapphire, or any other metal or ceramic material with suitable temperature resistant properties. In some embodiments, the body 40 includes a relatively thin external sleeve 56, described below (FIG. 3B).

As shown in FIGS. 2 and 4, the insert 38 and body 40 are both cylindrical in shape. The insert 38 is received in an opening 42 extending from one end of the body (FIGS. 2 and 3A). The insert 38 is preferably press-fit into the body 40 to form the assembled rotating disk electrode (FIG. 2). The insert 38 may include a tapped section (not shown) to facilitate the pressing process with a self-guiding and aligning function. The insert diameter $D_i$ is closely machined such that it is slightly larger than an inner diameter $D_{ib}$ of the body (FIGS. 3A and 4). The inner diameter $D_{ib}$ of the insert opening 42 of the body 40 and the outer diameter $D_i$ of the insert 38 are sized with very close tolerances to prevent gaps between the insert and body within the temperature range for intended measurement, as described in detail below. The tolerances are also tightly controlled to prevent cracking of the body 40 in applications in which a brittle material such as ceramic is used for the body.

The major design principles of one embodiment of a high temperature rotating disk electrode of the present invention are outlined in the following, intended to facilitate the understanding of this invention without limiting the scope of the invention. There are essentially two sets of conditions to be met by the high temperature rotating disk electrode. The first is the processing conditions, including the range of processing temperatures and processing environment. The second is the measurement conditions, including the range of measurement temperatures and electrochemical environment. The material choice of the insert 38 is mainly driven by the application, i.e., depending on the electrochemical measurement to be performed, and further constrained by the measurement as well as the processing conditions. The body material can be either electrically conductive, such as metal or graphite, or insulating, such as ceramic. If it is electrically conductive, then an electrically insulating sleeve 56 is required. If the body is electrically insulating, then the sleeve 56 is not necessary unless the body material is not electrochemically inert under the measurement conditions or not chemically inert under the processing conditions. Since at least a portion of the outer diametric surface and the front surface of the body 40 is in contact with the liquidus electrolyte 26 during measurement, it is desired that these surfaces are electrically insulating and electrochemically inert under the measurement conditions. Since all the surfaces of the RDE 20 may be exposed to the processing environment, it is desired that these surfaces are chemically inert to the processing conditions. In addition, all of the materials involved, i.e., insert 38, body 40, and sleeve 56 (if any), should maintain their mechanical integrity under measurement as well as the processing temperatures. Furthermore, the materials are chosen such that there are no undesirable reactions which occur among the insert 38, body 40, and sleeve 56 (if any) under the two sets of temperatures. As an example, one preferred construction of the RDE 20 is to use glassy carbon (also known as vitreous carbon) as the insert 38, graphite as the body 40, and CVD grown pyrolytic boron nitride (PBN) for the sleeve 56, as is later described for one embodiment.

Upon choosing the materials, the next major step is to determine the critical dimensions, i.e., $D_i$ and $D_{ib}$, and the associated tolerances, as a whole referred to herein as Critical Dimension (CD) (FIGS. 3A and 4). In one embodiment, there are three sets of constraints regarding CD. First, the insert needs to be press fit into opening 42 of body 40, typically under room temperature condition. If the fit is too loose, the insert 38 may detach from the body 40 during normal handling of the unit, which is undesirable. If the fit is too tight, the body may be damaged during the fitting process. Second, the fit needs to maintain a liquid tight seal in the entire range of measurement temperatures. Third, the unit needs to withstand the stress (if any) induced by thermal mismatch in the entire range of processing as well as measurement temperatures. Further details are provided below. One alternative to avoid the CD constraints is to use adhesive to attach and form the liquid tight seal between insert 38 and body 40. However, most common adhesives are polymeric in nature, which limits the temperature range. Certain cement adhesives can withstand high temperatures, but they typically do not perform well under repeated thermal cycling and may introduce electrochemical contamination during measurement.

Referring now to FIG. 3A, the body 40 includes a longitudinal opening 46 for receiving a motor drive shaft 50 (shown in FIG. 7A and described below). The body 40 also includes one or more radial openings 52 (one shown) extending from an outer surface of the body 40 to the shaft opening 46 for receiving a locking pin or set screw for holding the shaft 50 and rotating disk electrode 20 together (FIG. 3A). It is to be understood that other coupling means may be used to connect the shaft 50 to the RDE 20, without departing from the scope of the invention.

A number of different methods are described below for making different embodiments of the rotating disk electrode 20. Preferred embodiments include a body 40 which is precision machined to form a tubular member having a relatively thick wall (FIG. 3A). In some embodiments, the tubular member (or rod) is subjected to a coating or film growth processes (described below) to form the sleeve 56 on the outer surface and end faces of the body (FIG. 3B). If a tubular member is used (rather than a rod), the inner surfaces (e.g., openings 42 and 46) of the tubular member are preferably protected during the coating process so that they are not covered by the sleeve material. The sleeve 56 formed by the coating or growth process provides electrical insulation and chemical/electrochemical resistance. In other embodiments, the body 40 is formed without a sleeve 56 and has common material throughout.

After the body 40 is completed, the insert 38 is press fit into the body to create a liquid tight seal between the insert and the body. The assembled rotating disk electrode 20 may be annealed to above its rated maximum temperature to settle the insert 38 within the body before final polishing. One end surface of the body 40 and corresponding exposed end surface of the insert 38 are mechanically polished to form a seamless surface perpendicular to the rotation axis $R_A$ of the rotating disk electrode 20 (FIGS. 1 and 2). The polished end face provides a planar contact surface for exposure to the liquidus electrolyte during measurement.

As discussed briefly above, the body 40 is formed at least partially from an insulating material which is electrochemically inert to the liquidus electrolyte 26 used in the cell 18. In a preferred embodiment, the body 40 is formed at least partially from pyrolytic boron nitride (PBN). Other suitable materials include alumina, quartz, sapphire, aluminum, stainless steel, ceramic materials, or other materials which have the appropriate temperature, thermal expansion, and chemical compatibility requirements. The body material is preferably selected such that the thermal expansion coefficient is close to that of the material selected for the insert 38. In the embodiments in which the material of the inner portion of the body 40 is different than the material of the insert 38, the thermal expansion of the body is preferably larger than the thermal expansion of the insert so as to allow high temperature processing, since in typical applications, processing temperatures are higher than measurement temperatures.

The following provides a description of materials and methods used in making different embodiments of the rotating disk electrode 20. It is to be understood that these are provided as examples and that other materials and methods may be used without departing from the scope of the invention.

A method of producing a rotating disk electrode 20 of a preferred embodiment is shown in the flowchart of FIG. 5. A graphite rod is first machined to the appropriate diameter and length (step 60). The rod is then subjected to a CVD (chemical vapor deposition) or other suitable process to grow a pyrolytic boron nitride (PBN) layer having a typical thickness of about 0.1 mm to about 1.5 mm (step 62). Since the rod typically needs to be fixed in a growth chamber, one end surface of the rod may not be completely coated. The coated rod is then precision machined to include opening 42, preferably from the end surface with full coating coverage, opening 46, and opening 52 to form the body 40 shown in FIG. 3A (step 64). An insert 38 is press fit into the insert opening 42 in body 40 (step 66). The insert 38 is preferably a glassy carbon insert, more preferably a high temperature grade glassy carbon insert (e.g., Alfa Aesar Type II Glassy Carbon). The exposed end face of the insert 38 is grounded so that it is generally flush with the end surface of the body 40 and the entire surface is then polished to form the rotating disk electrode 20 (step 68). An annealing process, in which the unit is placed in a vacuum furnace and heated to a certain high temperature to settle the insert, is preferably carried out after grounding but before the final polishing. The critical dimensions and tolerances are preferably set to satisfy the following:

$$D_{i,min} > D_{ib,max}; \quad D_{i,min} = D_i - \tau_{i,-}; \quad D_{ib,max} = D_{ib} + \tau_{ib,+}; \qquad (1)$$

$$\frac{D_{i,max} - D_{ib,min}}{D_{ib,min}} < 0.1\%; \quad D_{i,max} = D_i + \tau_{i,+}; \qquad (2)$$

$$D_{ib,min} = D_{ib} - \tau_{ib,-};$$

The first condition assures that the insert and the body shall minimally have zero clearance fit (at room temperature condition) to meet the liquid tight seal requirement. The second condition is to assure the fit is within the stress limit at room temperature. The CVD formed boron nitride sleeve 56 provides excellent electrical insulation and is chemically inert to above 2500° C. (except in a fluorine-containing environment). The graphite core typically has a CTE (coefficient of thermal expansion) of about $2 \times 10^{-6}$ K$^{-1}$, and that of PBN is about $2.5 \times 10^{-6}$ K$^{-1}$, which is slightly smaller than that of the Type II glassy carbon, $2.6 \times 10^{-6}$ K$^{-1}$. Since the insert 38 is press fit at room temperature into the body 40 to form the liquid tight seal and the insert expands slightly faster than the sleeve which is weaker than the core, the stress increase is minimal at higher temperatures. In addition, PBN typically exhibits higher tensile strength at elevated temperature relative to room temperature. Thus, the maximum allowable working temperature is essentially identical to that of the processing temperature (i.e., about 2500° C.). The components are also easy to machine, resulting in lower production cost, while providing high performance. Furthermore, the relatively thick sleeve 56 allows for multiple reuse of the device. In a preferred embodiment, $D_{ib}$ is nominally set to 5 mm with a circularity specification of 0.002 mm. After opening 42 is machined, the actual $D_{ib}$ is measured to a precision of 0.001 mm or better. The insert 38 is then machined with $D_i$ set to be the maximum measured $D_{ib}$ plus the associated measurement error plus 0.002 mm and with circularity specification of 0.002 mm.

In one preferred embodiment, the graphite core is machined to have a cylindrical shape with two diametrical sections. The larger one is chosen such that, after PBN growth and precision machining, it will become the desired outer diameter of body 40. The diameter of the smaller section is chosen to be equal to the desired $D_i$ (FIG. 3A). The small section also serves to mount the graphite core in a growth chamber. After PBN growth, this section is cut out to expose the core and form the front end surface of the electrode. The exposed graphite surface functions as the electrode surface. Since there is no CD requirement in this process, the manufacturing cost is further reduced. Furthermore, the graphite surface typically exhibits significantly higher effective surface area in comparison with metal or glassy carbon inserts, it is thus advantageous in certain applications requiring higher surface area or larger current carrying capacities. Since the CTE of the graphite core is slightly smaller than that of PBN coating, it is preferred to have thin PBN coating, typically from 0.05 mm to 0.5 mm to avoid detachment of the core from the coating.

Figure 6:
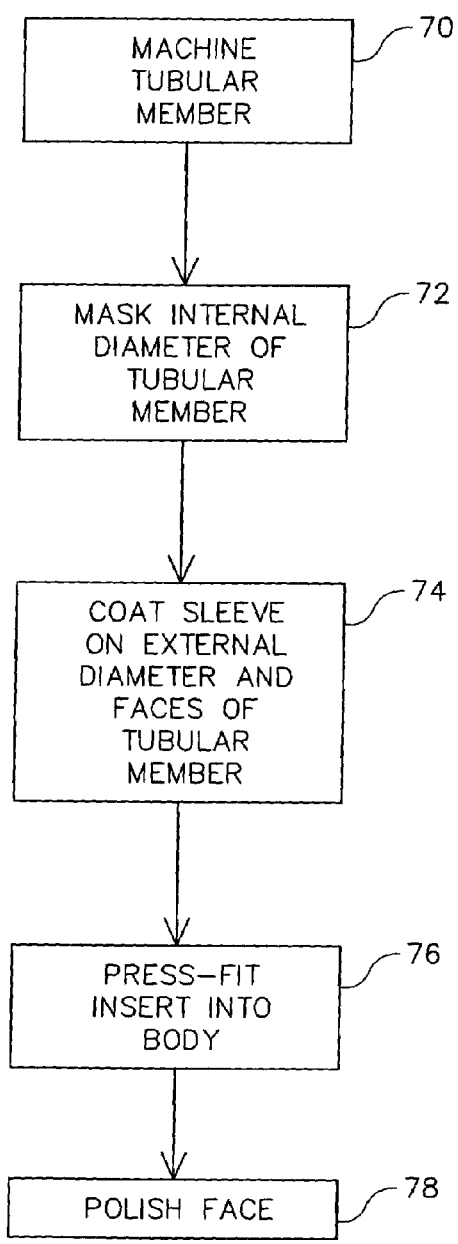
FIG. 6 is a flowchart illustrating a second process for manufacturing the rotating disk electrode of FIG. 2.

A process for forming a second embodiment of the rotating disk electrode 20 is shown in the flowchart of FIG. 6. In the second embodiment, a rod or a tube is first machined to form the tubular member of FIG. 3A (step 70). The tubular member may be formed, for example, from an aluminum metal. Before forming an outer sleeve 56 on the tubular member, the inner surfaces (openings 42 and 46) of the tubular member are preferably masked (step 72). An outer sleeve material is coated on the external surfaces of the tubular member (step 74). The outer sleeve 56 may be formed, for example, by a commercial process known as clear hard anodizing. The clear hard anodizing results in a thin and dense layer of $Al_2O_3$ with typical thickness of 0.5 µm to 100 µm on the exposed surfaces. The insert 38 is then pressed into the insert opening 42 to complete the rotating disk electrode 20 (step 76). The insert 38 may be formed, for example, from glassy carbon and preferably Type I glassy carbon, which has a CTE of $3.5 \times 10^{-6}$ $K^{-1}$. The end surface of the RDE 20 is mechanically polished to form a seamless surface orthogonal to the cylinder (step 78). The CD is essentially the same as before, except the second condition ((2) above) is relaxed to 0.2%, and it is preferred to have the fit close to the stress limit. This method provides low production cost with reasonably good performance. Since the melting point of aluminum is about 660° C., the upper limit of the processing temperature that the rotating disk electrode 20 can be exposed to is about 600° C. Furthermore, since the aluminum CTE is about $23.5 \times 10^{-6}$ $K^{-1}$, the working temperature is limited to about 100° C. If a metal or graphite insert 38 is used instead of glassy carbon, the stress budget is increased at least 0.4%, allowing higher stress state at room temperature and consequently higher working temperature limit of the electrode. Platinum, gold, and several other metals have CTEs that are closer to aluminum than carbon, and will further increase the working temperature limit. Due to the thin sleeve layer 56, the reusability of this RDE 20 is limited, if repolishing of the end face is required, rather than a chemical cleaning process. However, the low cost of the device may render recycling unnecessary.

In a third embodiment, the tubular member is formed from a steel or stainless steel metal. The manufacturing process is similar to that shown in the flowchart of FIG. 6 and described above for the second embodiment, however, the materials and coating process are different. The sleeve is formed by a process known as Silcosteel®. As previously discussed, the inner surfaces of the tubular member may be masked during the process. This method results in a thin layer 56 of $SiO_2$ with typical thickness of 0.5 um or less on the exposed surfaces. The insert 38 is then pressed into one end of the body to complete the RDE 20. The use of steel raises the processing temperature to over 1000° C. However, the machining and film forming process costs are higher than with the second embodiment described above. The CTE of stainless steel is lower than aluminum at about $16 \times 10^{-6}$ $K^{-1}$, allowing for higher working temperature of the rotating disk electrode 20. The ratio of the tensile strength versus elastic modulus of the metal is also higher than aluminum, resulting in higher stress budget, which can then be spent either on looser tolerance control, providing lower production cost, or higher working temperature limit. Since the sleeve 56 is typically very thin, precaution should be taken in polishing the end face. If the insert 38 is formed from metal or other alloy, then the thermal expansion coefficient mismatch is dramatically reduced, and the working temperature is significantly raised.

In a fourth embodiment, the rotating disk electrode body 40 is formed from a ceramic material such as alumina, silica, sapphire, or other suitable ceramics. Since the RDE body 40 itself is electrically insulating and chemically inert, no sleeve is necessary. The body 40 is first machined, the insert 38 is then press-fit into one end of the body, and the end faces of the insert and body are grounded and polished, as previously described. For this embodiment, tight control of mechanical tolerances of relevant dimensions as well as aligning and pressing details are maintained due to the material differences between the insert 38 and body 40 which are now in contact with one another. In general, this results in higher manufacturing costs. This device, however, can handle greater than 1000° C. processing temperature, due to the intrinsic properties of the materials and the small or negative thermal expansion coefficient mismatch. This also allows the working temperature to be similar to the processing temperature. This rotating disk electrode 20 is reusable with mechanical re-polishing and has a very long lifetime, since there is no sleeve involved. Furthermore, the insert 38 can be replaced as many times as desired, providing practically unlimited lifetime of the unit.

Figure 7A:
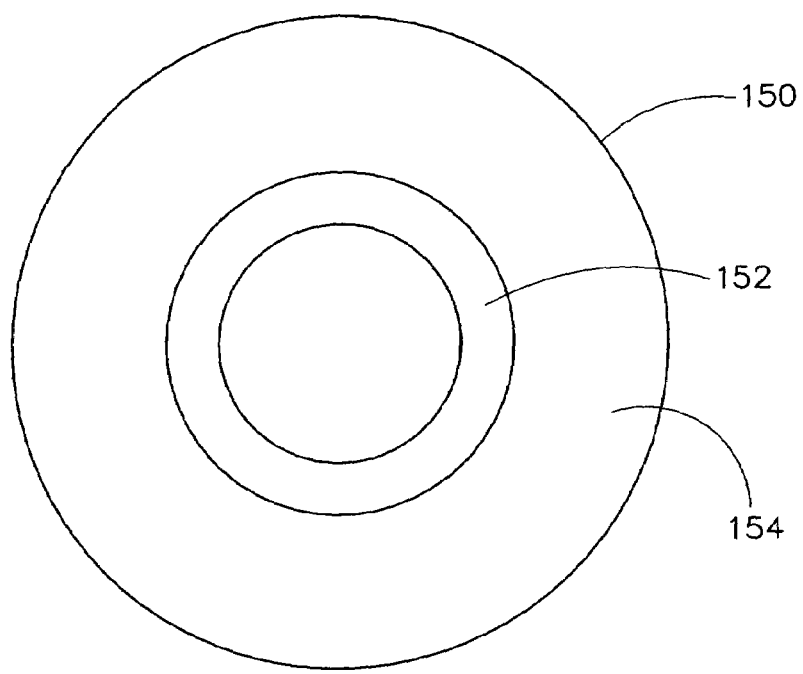
FIG. 7A is an end view of a rotating disk electrode having a ring shaped insert.
Figure 7B:
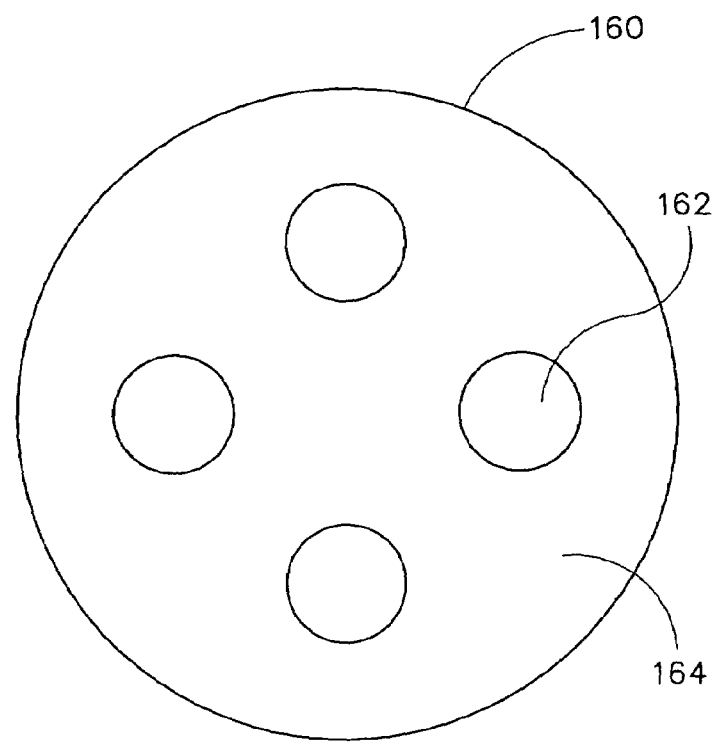
FIG. 7B is an end view of a rotating disk electrode containing a plurality of cylindrical inserts.

FIGS. 7A and 7B illustrate alternative embodiments of the rotating disk electrode of FIG. 2. FIG. 7A is an end view of a rotating disk electrode 150 comprising an annular ring insert 152 formed from an electrode material (i.e., electrically conducting material with desired electrochemical properties) and a body 154 formed from a material capable of withstanding high temperatures. The rotating disk electrode 150 may contain any number of inserts 152 which are radially offset and electrically isolated from one another. The rings may also be formed as disks and axially offset from one another. The body 154 is formed with an annular opening to receive the insert 152 which is in contact with contact pins (described below with respect to the rotating disk electrode of FIG. 2). Alternatively, the body 154 may be formed with a recess (not shown) to receive a ring shaped insert 152. The insert 152 is in contact with contact pins and another insert made from electrically insulating and chemically inert material, which fills a central void of the insert 152.

FIG. 7B is an end view of a rotating disk electrode 160 containing a plurality of inserts 162. The inserts 162 may be shaped and manufactured the same as inserts 38, described above, for example. The body 164 is formed from a solid material capable of withstanding high temperatures and electrically isolates each of the inserts 162 from one another. The electrode 160 may also be used in low temperature operations for which the body 164 may be constructed of Teflon, or other suitable material. FIG. 7B illustrates a rotating disk electrode containing four inserts 162, however, it is to be understood that any number of inserts may be used.

FIG. 8A shows one example of a rotating disk electrode drive shaft 50 which is configured for insertion into the shaft opening 46 at the end of the body 40 (FIG. 3A). The drive shaft 50 is a precision machined body which is mechanically connected to a motor shaft 82 (FIGS. 8A and 9). The drive shaft 50 may be machined, for example, from stainless steel. The rotating disk electrode 20 and drive shaft 50 are preferably precision machined such that the RDE may be slip fit onto the shaft. This provides mechanical integrity while allowing for attachment and detachment of the rotating disk electrode 20 from the shaft 50. In a preferred embodiment, the drive shaft 50 includes a tapped section 80 to facilitate coupling or decoupling with a self-guiding and aligning function. The electrode 20 and drive shaft 50 are preferably coupled in a detachable arrangement.

The shaft 50 is configured to cooperate with a metallic spring 90, which provides one path of electrical contact between the insert 38 or effective insert (i.e., where insert is formed as part of body) and end of the drive shaft 50. The shaft 50 may also be configured to cooperate with a spring loaded contact pin 84 (FIG. 8B) residing through the center axis of the shaft, which provides another path of electrical contact to the insert 38 or effective insert. In one embodiment the pin 84 may be, for example, a Pogo pin. The pin 84 is electrically insulated from the shaft body by, for example, a TFE (Tetrafluoroethylene) or ceramic sleeve 86. The contact pin 84 and shaft body are electrically connected to a hollow type slip ring 88 to bring the electrical contacts out to the measurement system. In a preferred embodiment, the shaft 50 carries the current and the contact pin 84 is used for voltage sensing of the rotating disk electrode 20. As shown in FIG. 1, two connecting wires 30 are coupled to the potentiostat 32 and rotating disk electrode 20 to provide two separate contact points. The separation of voltage path from current path is important in low noise measurement applications, especially where high electrical current is involved.

The contact pin 84 contacts the back end of the insert 38 to provide voltage sensing. The spring loading of the contact pin 84 assures good electrical contact between the pin 84 and insert 38. The spring 90, preferably made of a copper containing alloy, contacts the back end of the insert 38 and the shaft body 50. The spring force assures good electrical contact of the shaft body 50 and insert 38. The spring force tends to push the rotating disk electrode 20 out and locking pins are inserted into the radial openings 52 of the body and aligned opening 92 of the shaft 50 to lock the electrode and the shaft. Two locking pins are preferred, however, any number may be used. The locking pin may be any suitable material which assures good mechanical integrity and chemical inertness under the measurement conditions.

As shown in FIG. 10, a protective sleeve or jacket 94 may be inserted over the rotating disk electrode 20 and shaft assembly. The jacket 94 is preferably formed from TFE, PEEK, alumina, or other suitable material which provides required chemical and mechanical properties. The jacket 94 protects the joints of the RDE 20 and shaft 50 and locking pins from electrolytes as well as the centrifugal forces experienced by the locking pins during high speed rotations. As shown in FIG. 10, in some embodiments, the jacket may include a lip 96. The lip 96 functions to guide the electrolyte liquid and minimize liquid splitting during high-speed rotation of the assembly.

As discussed above, the rotating disk electrode 20 may be used to test different coating materials and methods of applications. For example, physical vapor deposition, electroplating, liquid dispensing of chemical solution, or powder impregnation, may be used to apply a coating to the exposed end of the insert of the electrode to form the electrolytic surface.

Figure 11:
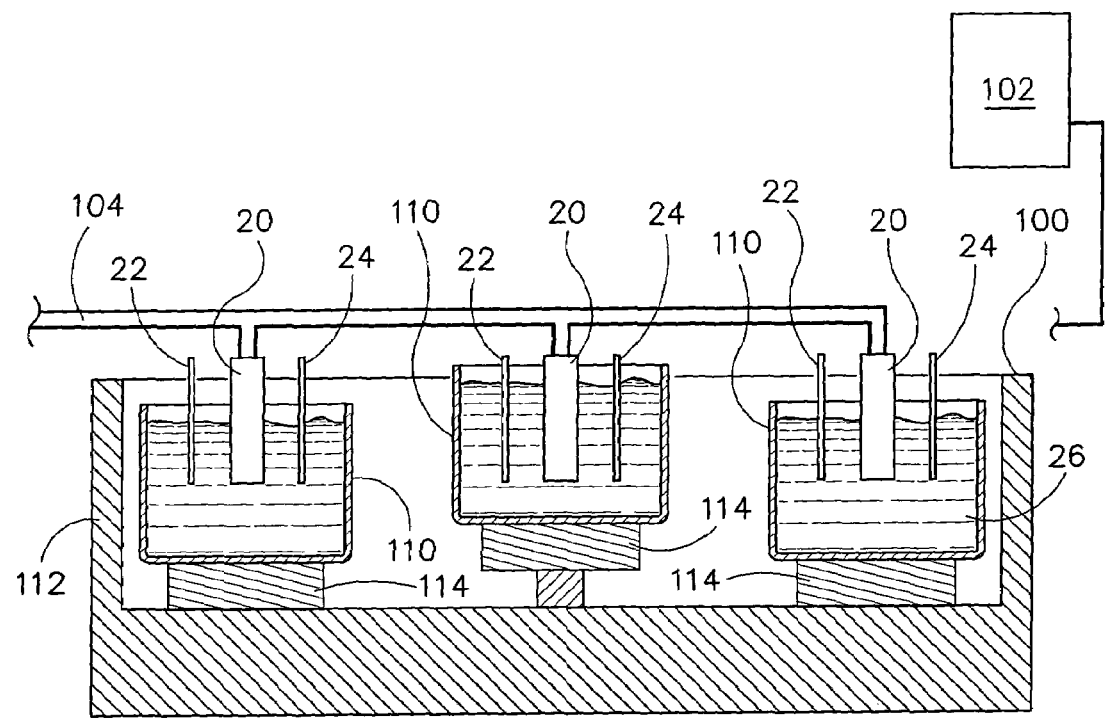
FIG. 11 is a schematic of a parallel electrochemical analysis system configured to hold a plurality of cells and change the depth of insertion of a working electrode in liquidus electrolyte of the individual cells.
Figure 12:
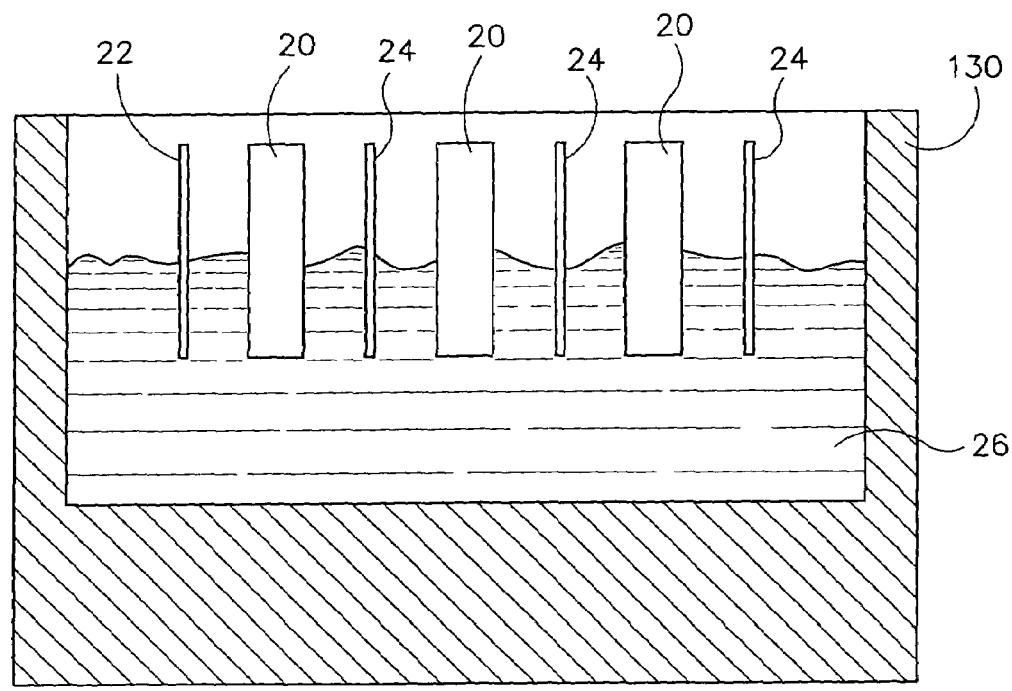
FIG. 12 is a schematic of a parallel electrochemical analysis system having a plurality of electrodes contained within one cell.

Once the coating is applied, the rotating disk electrode 20 is coupled to the shaft assembly and placed in a cell, such as shown in FIG. 1 or an electrochemical testing system such as shown in FIGS. 11 and 12, and described below. After testing and analysis is complete, the end face of the rotating disk electrode 20 may be mechanically polished or chemically cleaned, and a new coating may be applied. As previously discussed, there may be limitations to the number of times that the rotating disk electrode 20 can be reused based on the design of the RDE and the methods of cleaning.

FIG. 11 is a schematic illustrating a parallel electrochemical screening system 100 comprising a plurality of electrochemical cells 110 grouped together and coupled to an automated electrode positioning system (not shown). Each cell includes a cavity for containing a liquidus electrolyte and a first working electrode 20 having at least one electrolytic surface at least partially within the cavity. The first working electrode 20 includes a body and an insert supported by the body and may be, for example, one of the high temperature rotating disk electrodes 20 described above, or any other suitable device having an electrically insulating body and an electrically conducting insert supported by the body. As previously discussed, the electrolytic surface of the working electrode is formed on or integral with the insert. The system 100 provides a means for evaluating a large number of diverse materials in a short time. Each cell 110 is similar to the cell 18 shown in FIG. 1 and includes working electrode 20, reference electrode 22, and counter electrode 24. The individual cells 110 may have their own control and measurement channel or individual instrument (not shown) or may be controlled as a group. For example, the rotating disk electrodes 20 may be driven by a common drive system or shaft 104 (shown schematically in FIG. 11). The drive system is detachably coupled to one or more of the working electrodes (or a portion of the working electrode) for effecting relative motion between the electrolytic surface of the working electrode and a bulk portion of the liquidus electrolyte 26. The cells 110 are grouped together in a control box 112 configured for holding two or more cells. Each cell is positioned on a platform 114 movable in a generally vertical direction. The platform 114 may be individually or collectively driven, for example, by one or more pneumatic actuators (not shown) or any other suitable driving means. By changing position of the cell 110, the insertion depth of the electrodes 20, 22, 24 can be changed independently for each cell. The motion of each platform may be controlled by a common processor 102 along with a potentiostat so that a series of test can be performed in an automated fashion. The user provides the processor 102 with operating parameters using a software interface. Typical operating parameters include speed of rotation (individual rotation of each electrode 20 or rotation as a group), depth of insertion of the electrodes, time of rotation (on and off control), solution, and potentiostat control. The processor 102 may also receive data from the electrodes or monitor the solution and perform calculations on the data.

The plurality of cells 110 may be used, for example, to conduct corrosion studies of a specific metal alloy (e.g., stainless steel). The same metal alloy may be used for each insert of the electrodes 20. The electrodes 20 are inserted into different cells, each containing, for example, different corrosion inhibitors to evaluate the corrosion properties of the metal alloy.

FIG. 12 illustrates an alternative parallel electrochemical testing system 130. The system 130 includes an electrochemical cell containing a plurality of working electrodes (e.g., RDE 20) and at least one counter electrodes 24, and preferably, at least one reference electrode 22 all immersed in a common reservoir. The electrodes may be individually controlled or coupled to a multi-channel potentiostat. The cell shown in FIG. 12 includes three working electrodes 20, one reference electrode 22, and three counter electrodes 24. It is to be understood that any number of electrodes 20, 22, 24 may be used, without departing from the scope of the invention. Also, a common processor may be used to control the testing and collect data, as described above with respect to FIG. 11.

FIGS. 13, 14, 15, and 16 show a holder 170 for supporting an array of rotating disk electrodes, such as shown in FIG. 2. The holder 170 is configured to support the electrodes 20 during processing and allow for the detachment of the electrodes after processing is complete. The holder 170 allows the electrodes 20 to be positioned in an array format for synthesis by, for example, PVD techniques, the deposition of electrocatalyst inks, or by electrochemical deposition, as previously described, or any other process for depositing an electrochemical material. After processing, each electrode 20 is detached from the array and placed into a testing apparatus, such as described above. The detachable electrode arrangement provides an electrode array for combinatorial synthesis as well as processing, including high temperature synthesis, in-situ thermal processing, and post annealing. The array also simplifies characterization tasks, such as x-ray and electrochemical screening, which can be performed while the electrodes are in an array format.

The holder 170 includes a block 171, front plate (mask) 174, and back plate 180 which holds the RDEs in place. The holder block 171 includes a plurality of openings 172 extending from the front plate 174 to the back plate 180 (FIGS. 15 and 16). As shown in FIGS. 13-16, the holder block 171 and plates 174, 180 are generally circular in shape. However, other shapes and configurations may be used without departing from the scope of the invention. The holder 170 may be sized to correspond to different types of processing equipment (not shown) based on the specific process used to apply a coating to the exposed surface of insert 38 to form the electrolytic surface.

The openings 172 are sized for receiving the rotating disk electrodes 20. In one embodiment, the openings are configured such that the electrodes 20 are slip fit into the holder. For example, a diametric gap of 0.0005 to 0.001 inch may be provided between each of the electrodes 20 and holder block openings 172. For example, if the outer diameter of the electrode 20 is 12.00 mm, the inner diameter of each of the holder openings may be 0.4730+0.0005/−0 inch. As shown in FIGS. 13-16, the holder includes openings for receiving sixteen rotating disk electrodes 20, however, it is to be understood that the holder may be configured to hold any number of electrodes, without departing from the scope of the invention.

The material of the holder block 171 is selected based on the processing operation to be performed on the electrodes 20. For example, since PVD depositions are typically carried out in vacuum conditions, 300 series stainless steel may be used. Since liquid dispensing and ink printing are typically done in air, plastic materials such as PEEK or Teflon may be used and the openings 172 may be sized to be slightly smaller than the outside diameter of electrodes 20 for light press fitting of the electrodes 20 to the holder block 171. In applications in which the holder 170 is used for mechanical polishing and cleaning of the electrodes, an aluminum holder is preferred.

Figure 13:
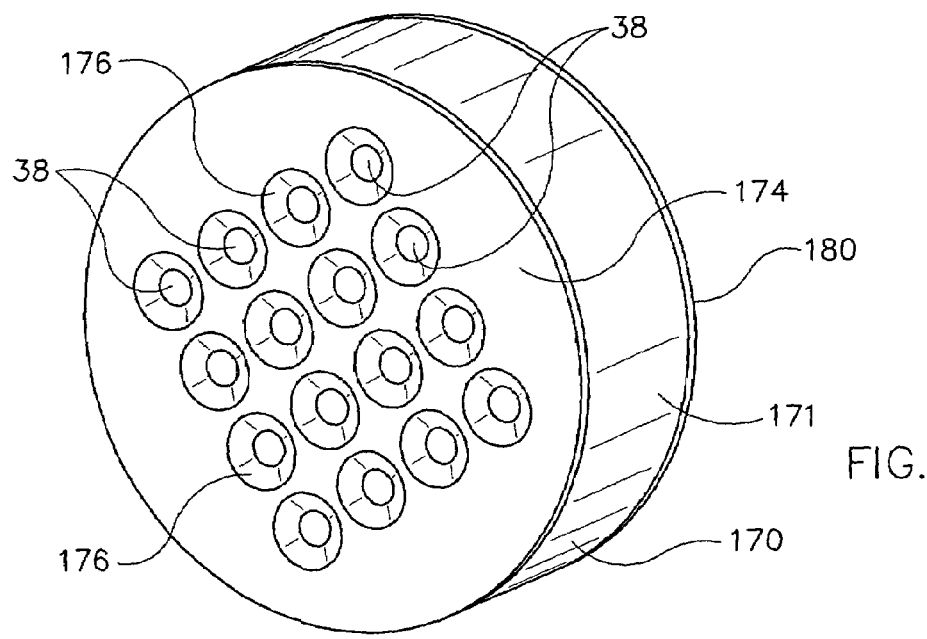
FIG. 13 is a front perspective of an electrode holder containing an array of rotating disk electrodes of FIG. 2.

The mask 174 includes a plurality of tapered openings 176 arranged to align with openings 172 in the holder block 171 (FIG. 13). The tapered openings are sized to expose only the insert 38 so that plating (coating) can be applied to the insert without being applied to the body of the rotating disk electrode 20. When a PVD process is used to deposit material onto the electrode, the mask 174 may be formed from metal (e.g., stainless steel), ceramics, glass, or silicon, for example. If the mask 174 is configured for use in a PVD application, the angle of the tapered opening is, for example, 120 degrees in a preferred embodiment, or between 90 degrees and 120 degrees as shown in FIG. 13.

The mask 174 may be formed from a single crystal silicon wafer. The openings for the silicon wafer are preferably rectangular in shape based on manufacturing processes. In one embodiment, the opening may have a tapping angle (total angle) of 70.529 degrees.

For applications using electrocatalyst inks to deposit materials onto the electrode, the mask 174 is preferably formed from hydrophobic materials, such as Teflon. The taper angle is preferably from 0 degrees (i.e., straight hole with sharp edge) to 90 degrees for liquid dispensing. For ink printing and aerogel spraying applications, any material which does not react with the ink or aerogel may be used. For these applications, the taper angle is preferably 120 degrees or greater to minimize obstruction of air flow or ink tip access. For electroplating or electrochemical screening, the mask 174 may not be needed since deposition only occurs on the electrode surface. It is to be understood that the materials and taper angles specified above are provided as examples, and other suitable materials which can withstand the temperatures required for processing the electrodes 20 may be used without departing from the scope of the invention.

Figure 14:
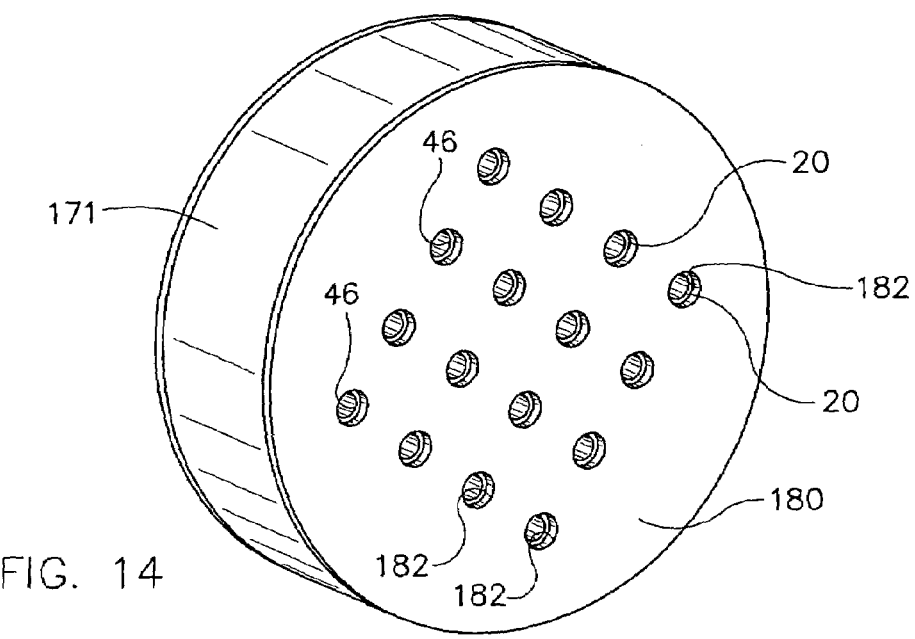
FIG. 14 is a back perspective of the electrode holder of FIG. 13 containing an array of the rotating disk electrodes.
Figure 15:
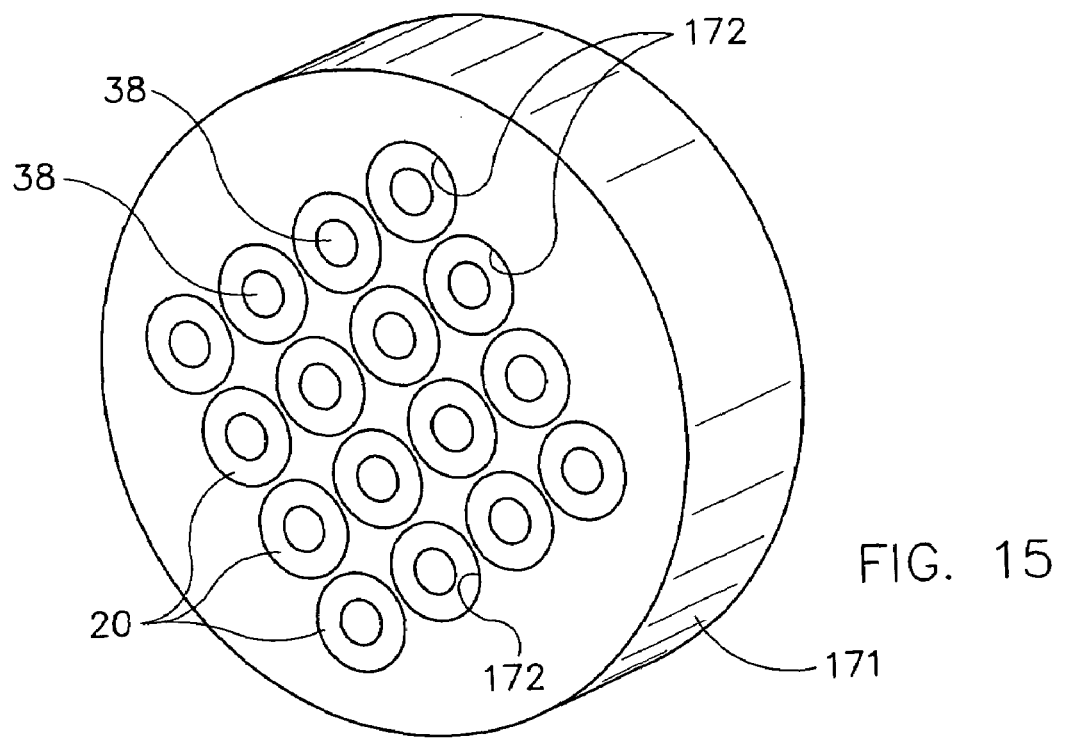
FIG. 15 is a front perspective of the electrode holder of FIG. 13 with a front plate removed.
Figure 16:
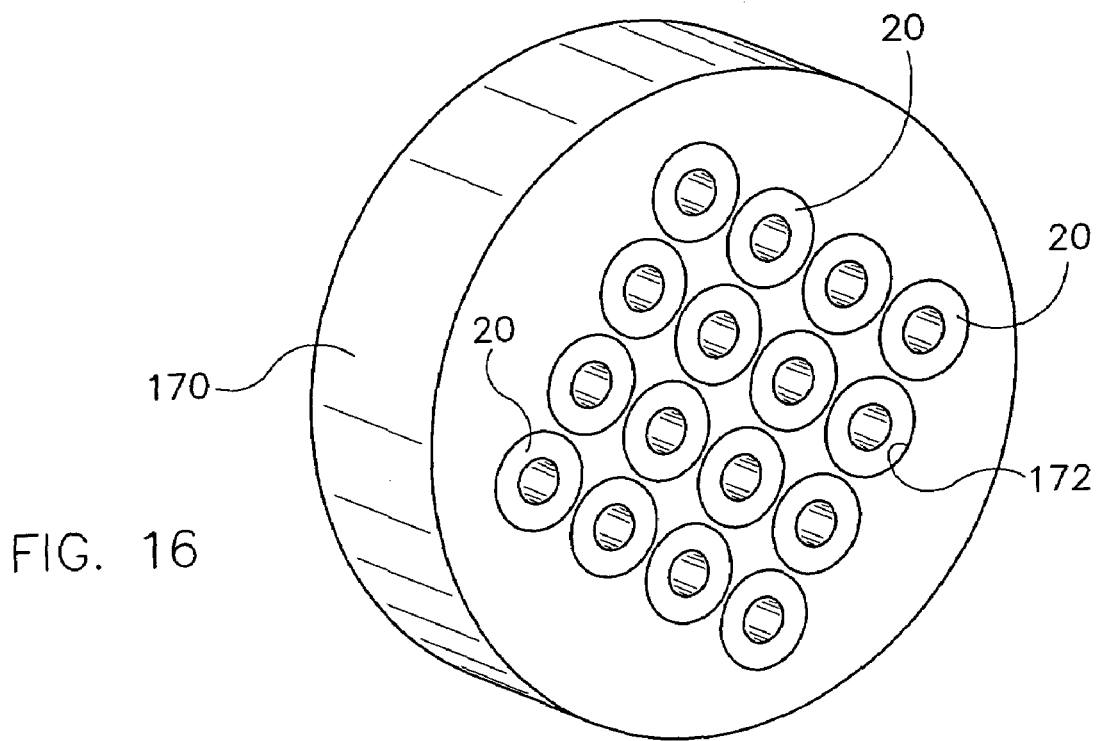
FIG. 16 is a back perspective of the electrode holder of FIG. 14 with a backing plate removed to show the rotating disk electrodes.

The back plate 180 includes a plurality of openings 182 aligned with openings 172 in the holder block 171 (FIGS. 14 and 15). The openings 182 provide vent passageways which allow the inner volume of the electrodes 20 to be pumped efficiently. The openings 182 also prevent virtual leaks of the assembled unit under vacuum conditions. For liquid dispensing, ink printing and aerogel spray, any suitable material may be used as long as the material does not react or contaminate the solutions or solvents used in the process. For vacuum applications, the back plate 180 is preferably made from stainless steel or OFHC (Oxygen-Free High Conductivity) copper, with stainless steel being the preferred material based on its durability. Copper provides better temperature uniformity but easily oxidizes in air.

The front plate 174 and back plate 180 are attached to the holder block by any suitable fastening means including fasteners (not shown). The fasteners may be formed, for example, from stainless steel for vacuum applications and for other applications, materials which are compatible with the processing environment. For vacuum applications, vented screws are preferably used. Alternatively, vent passages may be implemented directly on the holder to avoid virtual leaks. If the processing operation requires the front surface of the mask 174 to be essentially flat (i.e., screw heads cannot extend from a front surface of the mask), flat head screws or counter bores are preferably used. The holder 170 may also include dowel pins or other suitable devices (not shown) which are used to precisely locate the mask 174 with respect to the holder block 171.

After the electrode array has been inserted into the holder 170, the array may be immersed in electrolyte bath for electroplating or electrochemical screening, such as described, for example in U.S. Pat. Nos. 6,468,806 and 6,187,164, which are incorporated herein by reference in their entirety. The individual electrodes 20 of the array may be coupled to a potentiostat (e.g., multichannel or multiplexed) and parallel electroplating or electrochemical screening may be performed.

The following describes examples of use of the holder 170 in different processing operations. First, processing operations used to form the electrolytic surface on the exposed end of the insert 38 (FIG. 13) are described. Next, a primary screening process performed on the electrodes 20 while inserted in the holder 170 is described. It is to be understood that these are provided as examples and that variations in the processes or different processes may be used without departing from the scope of the invention.

As previously discussed, different types of PVD processes may be used to form the electrolytic surface on the insert 38. These processes include, but are not limited to, magnetron sputtering, pulsed laser deposition (PLD), thermal evaporation, and e-beam evaporation. In PVD deposition applications, the holder block 171, front plate 174, back plate 180, and electrodes 20 are first pre-cleaned by chemical and mechanical methods. The mask 174 is then mounted onto the holder block 171 and the electrodes 20 are inserted into the holder and placed against a back face of the mask 174. The back plate 180 is then mounted onto the holder block 171 to hold the electrodes 20 in place. The back plate 180 preferably retains some tension so that there are no gaps between the back surface of the mask 174 and mating front surfaces of electrodes 20 under all operating conditions, including elevated temperatures. The assembled unit is attached to a fixture inside a vacuum chamber of a PVD system (not shown) and the chamber is pumped down to a desired vacuum level, (e.g., $10^{-7}$ torr or greater). The fixture may optionally have heating and temperature control functions to raise and maintain the unit at desired temperatures. It may also be desirable to preheat the unit to a temperature higher than deposition temperature for degassing and preparing the working surface of the inserts 38. Heating may be accomplished by electric heaters through thermal conduction of the holder 170. Alternatively, infra-red (IR) lamps or light pipes may be used to direct IR photons directly to the inserts 38 from the back side of the electrode 20. The back plate openings 182 provide access to the back end of the inserts 38 via openings 46 (FIGS. 3A and 14). A light pipe mechanism has the advantage of allowing individual temperature control of individual electrodes in the array.

The deposition process may be serial, partial serial, parallel, or partial parallel, depending on the specific PVD system used and specific operation mode applied. Each of these modes is described below.

In serial deposition, one or more PVD sources are directed towards a screen plate (not shown) having one opening appropriately sized. The holder 170 and electrode array is mechanically moved with respect to the screen plate such that the desired electrode 20 is aligned with the opening of the screen. The sources are energized to create a flux with desired mixture of selected ingredients that passes through the screen and coats on the working surface (i.e., exposed end of the insert 38) of the desired electrode 20 to form the electrolytic surface (FIG. 13). It is preferable to have a flag near the screen to block the opening of the screen to allow the preparation of the PVD sources as well as to precisely control the exposure time of the flux to the electrode 20. Specialty gas, such as hydrogen, oxygen, nitrogen, ammonia, or $NO_2$, may be introduced to facilitate the deposition and reactions. Once the deposition process is complete, the opening is closed, the sources may be turned off, and the holder 170 and electrode array is moved (relative to the screen) to the next desired location deposition onto the next electrode 20. The temperature of the unit may also be adjusted accordingly. After all the coatings are applied, the holder 170 and electrode array may be optionally heated to a higher temperature for post-annealing for a desired period of time. Certain specialty gases, such as hydrogen, oxygen, nitrogen, ammonia, or $NO_2$, may be introduced into the vacuum chamber to facilitate the post-annealing or reactions. Upon finishing the post processing, the chamber is vented and flashed and the unit is taken out of the PVD system and screening or characterizations may be performed. Alternatively, the holder 170 and electrode array may be transported to a mobile load-lock system and transferred to a characterization system while maintaining a vacuum or other desired environment.

In partial serial deposition, the screen has more than one opening forming certain patterns, such as a row, double row, one or more columns, or one or more large openings. Consequently, more than one electrode 20 may be coated simultaneously in one coating procedure with predefined patterns. The predefined patterns may also be changed from one procedure to the next by changing the screen in-situ.

For a parallel deposition process, a PVD system such as one described, for example, in U.S. Pat. No. 6,364,956 (which is incorporated herein by reference in its entirety), in which the entire electrode array is exposed to the total flux, and each individual ingredient flux is individually controlled to create a library of different materials. Alternatively, multiple sources using natural gradient of individual source flux can be similarly implemented. The later method is known by those skilled in the art as a composition spread method.

In partial parallel deposition, a PVD system with one or more pairs of dynamic shutters may be used. The shutters are described in U.S. Pat. No. 6,045,671, which is incorporated herein by reference in its entirety. The deposition is carried out by depositing each ingredient material flux through an opening dynamically created by the dynamic shutters. The desired composition of each individual electrode 20 is achieved by superimposing multiple patterns of multiple ingredient films (superlattice-like deposition), as disclosed in PCT Patent Application No. WO0248841, which is incorporated herein by reference in its entirety.

The following describes a process for liquid dispensing solutions onto the electrodes 20 positioned in the holder 170. In liquid dispensing, a set of solutions is prepared and the holder 170 and electrode array are placed in a liquid dispensing machine. (See, for example, U.S. Pat. No. 5,985,356 and PCT Patent Application No. WO 00/17413, which are incorporated by reference herein in their entirety.) The solutions are drawn from individual containers and delivered to the working surface of each individual electrodes 20 in serial fashion. The unit is then dried at ambient or elevated temperature and desired environment, as has been previously discussed. The unit may then be subjected to high temperature and specific atmosphere for causing specific reactions, alloying or other physical or chemical processes. Alternatively, the unit may be disassembled after liquid dispensing and drying and each individual electrode 20 or groups of electrodes may then be subjected to a variety physical or chemical processes.

In an ink-printing process, ingredient solutions are pre-mixed and fed into an ink head (not shown), or dynamically mixed in the head, and then applied onto the working surfaces of electrodes 20 in serial fashion. Alternatively, multiple ink heads may be used. Each ink head is supplied with a one or more ingredient solution and all are directed towards the same working surface of an electrode 20 simultaneously or in an alternating fashion. Drying and post processing is similar to the liquid dispensing process described above.

For aerogel spray applications, multiple solutions are fed into and mixed at a spray head (not shown) and the relative ratios of ingredients are changed dynamically, and the aerogel flux is directed to each individual electrode surface in serial fashion. Alternatively, multiple spray heads can be used and each is individually controlled to create a desired total aerogel flux and the ingredient mixing occurs in air and on the surface. It is also feasible to use a single head or fire individual heads one or a few at a time to perform layer by layer deposition over the entire electrode array with pairs of dynamic shutters creating patterns of openings on the move. This process is similar to the partial parallel PVD deposition, described above, except that large numbers of repeated steps may not be necessary. In the later mode of operation, the solvent and environment is preferably controlled since the evaporation process may be slow with respect to the total deposition time to allow multiple ingredients to be thoroughly mixed on the surface (e.g., by diffusion mechanism). The holder 170 may also optionally be shaken during or after material delivery using, for example, ultrasonic techniques, to further promote the mixing before drying.

After processing of the electrodes is complete, a primary screen may be performed on the electrodes while still retained in the holder 170. For example, an electrical connection may be made to each individual electrode 20 in the array. With the front plate 174 removed (FIG. 15), the array may be partially immersed in an electrolyte bath such that the conductive portion of each of the electrodes 20 is exposed to the electrolyte. The electrodes 20 may be coated with a PVD layer or powder electrocatalyst, for example The array of electrodes 20 may be interfaced to a potentiostat (multichannel or single channel multiplexed) and in a conventional two or three electrode set-up, the materials on each electrode may be screened (electrochemically) for a property of interest such as for example electrocatalysis. One advantage of the present invention is that one or more electrodes that exhibit useful properties can be detached from the holder 170 and reassembled in an electrochemical screening cell for secondary screening. Therefore, the ability to use the electrodes 20 in array format (for primary screening) and to detach one or more of the electrodes for additional screening (e.g., secondary screening) offers the advantage that the material on the electrode does not need to be resynthesized for secondary screening.

It is to be understood that processing of the electrodes may also be performed without the holder 170. For example, electroplating may be performed with the electrodes mounted on the drive shaft and immersed in electrolyte, in which case, no holder is required. In an electroplating process each individual electrode 20 is mounted on its own drive shaft and immersed in its own electrolyte bath or immersed in one or more common baths in a group. Thus, the holder 170 is not needed. By controlling the voltage and current of each individual cell in combination with variation of electrolyte and sequence of operation parameters, a variety of materials and alloys can be plated onto the working surfaces of electrodes 20. After plating, each electrode 20 is dissembled from its drive shaft and washed. The electrodes 20 can then be subjected to further processing, individually or in groups. It is also possible to use the holder 170 and electrode array to carry out parallel electroplating such as described above for the parallel electrochemical screening.

The following example illustrates the principles and advantages of the invention. It is to be understood that the example is provided for illustrative purposes and is not intended to limit the invention in any manner.

A rotating disk electrode 20 was formed from a sapphire (single crystal) tubular shaped body 40 with a vitreous carbon (also known as glassy carbon) insert 38 (FIG. 2). The standard RDE profile was set as 35 mm in length and 12 mm in outside diameter. The inside diameter $D_{ib}$ of the body was nominally 4.800 mm with roundness 0.001 mm at the section for insert insertion. The actual $D_{ib}$ was measured after the machining of the body 40, and the matching insert 38 outer diameter $D_i$ was then machined to be $D_{ib,measured}$ + 0.010 mm (FIGS. 3A and 4) and the roundness was controlled to 0.001 mm. The insert 38 was mechanically pressed into the body 40 and the end surface was grounded to flush. The assembled unit 20 was then put into a vacuum furnace for annealing. The vacuum level of the furnace was at least 5×10−5 torr. The heating rate was 5K/min and ramped up to 700° C. This temperature was held for at least one hour and the unit 20 was then cooled down at the rate of 5K/min. The end surface was then fine polished to have better than an 8 micro inch finish. The electrical characteristics of the RDE tip based on Sapphire/Glassy Carbon detailed above was compared with that of a conventional RDE Tip based on a Teflon/Glassy Carbon RDE.

The exposed end face of the insert was then coated with an electrocatalyst powder according to the following. A C/Pt electrocatalyst was applied to the tip of both the high temperature rotating disk electrode (RDE) and a conventional Teflon/Classy Carbon rotating disk electrode as is commonly used in the art (see, Rotating disk electrode measurements on the CO tolerance of a high-surface area Pt/Vulcan carbon fuel cell electrocatalyst, Schmidt et al., Journal of the Electrochemical Society (1999), 146(4), 1296-1304; and Characterization of high-surface-area electrocatalysts using a rotating disk electrode configuration, Schmidt et al., Journal of the Electrochemical Society (1998), 145(7), 2354-2358). Platinum supported on carbon black is commercially available from companies such as Johnson Matthey, Inc., of New Jersey and E-Tek Div. of De-Nora, N.A., Inc., of Sommerset, N.J.

The supported electrocatalysts on the rotating disk electrodes was prepared by depositing an aqueous-based ink that comprises the support electrocatalyst and a NAFION solution on a glassy carbon disk. The concentration of electrocatalyst powder in the NAFION solution was about 1 mg/mL. The NAFION solution comprised the perfluorinated ion-exchange resin, lower aliphatic alcohols and water, wherein the concentration of resin is about 5 percent by weight. The NAFION solution is commercially available from the ALDRICH catalog as product number 27,470-4. The conventional glassy carbon electrode was 5 mm in diameter and polished to a mirror finish. Conventional glassy carbon electrodes are commercially available, for example, from Pine Instrument Company of Grove City, Pa. An aliquot of 10 µL electrocatalyst suspension was added to the exposed glassy carbon surface for both the RDE and the conventional RDE and allowed to dry at room temperature for 30 minutes.

After being dried, the RDE was attached to the driving shaft 50 of FIG. 8A as disclosed. The conventional rotating disk electrode was threaded onto an adaptor which was then attached to the driving shaft. The adaptor was made from stainless steel and one section has the same profile as that of the RDE and another section has a ¼-28 thread that accepts the conventional RDE.

After assembly, the RDE tip was immersed into an electrochemical cell comprising an aqueous 0.5 M $H_2SO_4$ electrolyte solution maintained at room temperature, a Mercury/Mercury Sulfate Reference Electrode and a Pt Mesh counter electrode. The electrochemical cell and RDE apparatus was interfaced to a commercial potentiostat for electrochemical measurements. The electrochemical cell was purged of oxygen by bubbling argon through the electrolyte for about 20 minutes. Measurements were taken while the electrodes were stationary and also during rotating the electrode from about 400 rpm to 6000 rpm. One particular electrochemical test comprised cyclic voltammetric measurements while purging the electrolyte with argon. Specifically, measurements comprised two hundred consecutive potential sweeps starting from 0V to about +0.35V vs Mercury/Mercury Sulfate (MMS) Reference Electrode then to about −0.65V vs MMS and back to 0V vs MMS at a scan rate of about 200 mV/s followed by two consecutive potential sweeps starting from 0V vs MMS to about +0.35V vs MMS then to about −0.65V vs MMS and back to 0V vs MMS at a rate of about 50 mV/s. The above tests result in conditioning of the Pt supported electrocatalyst and more specifically, the slow scan rate measurements allow for the evaluation of the electrochemically active area of the electrocatalyst. In summary, essentially identical electrochemical results were obtained from supported electrocatalysts applied to the HTRDE and the conventional Teflon/Glassy Carbon RDE both with the stationary electrode and for electrode rotation up to approximately 6000 rpm.

Although the present invention has been described in accordance with the embodiments shown, one of ordinary skill in the art will readily recognize that there could be variations made to the embodiments without departing from the scope of the present invention. Accordingly, it is intended that all matter contained in the above description and shown in the accompanying drawings shall be interpreted as illustrative and not in a limiting sense.

What is claimed is:

1. An apparatus for evaluating an electrochemical reaction, the apparatus comprising:
   an electrochemical cell comprising a cavity for containing a liquidus electrolyte, a first working electrode having at least one electrolytic surface at least partially within the cavity, and a counter electrode having at least one electrolytic surface at least partially within the cavity, the first working electrode comprising a body and an insert supported by the body, each of the insert and the body consisting essentially of a high-temperature material allowing for preparation or processing of the at least one electrolytic surface at a temperature of at least 2000° C.; and
   a drive system detachably coupled to the first working electrode or a portion thereof for effecting relative motion between the at least one electrolytic surface of the working electrode and a bulk portion of the liquidus electrolyte.

2. The apparatus of claim 1 wherein the first working electrode is a rotating disk electrode.

3. The apparatus of claim 1 wherein the at least one electrolytic surface is formed on or integral with the insert.

4. The apparatus of claim 3 wherein the first working electrode comprises at least two electrolytic surfaces, each of said at least two electrolytic surfaces being electrically-isolated from one another.

5. The apparatus of claim 1 wherein the at least one electrolytic surface of the first working electrode is formed from a physical vapor deposition coating.

6. The apparatus of claim 1 wherein the insert is formed from carbon.

7. An apparatus for evaluating an electrochemical reaction, the apparatus comprising:
   an electrochemical cell comprising a cavity for containing a liquidus electrolyte, a first working electrode having at least one electrolytic surface at least partially within the cavity, and a counter electrode having at least one electrolytic surface at least partially within the cavity, the first working electrode comprising a body formed from graphite and an insert supported by the body, each of the insert and the body consisting essentially of a high-temperature material allowing for preparation or processing of the at least one electrolytic surface at a temperature of at least 300° C.; and
   a drive system detachably coupled to the first working electrode or a portion thereof for effecting relative motion between the at least one electrolytic surface of the working electrode and a bulk portion of the liquidus electrolyte.

8. The apparatus of claim 7 wherein the body is coated with boron nitride.

9. The apparatus of claim 7 wherein the high-temperature material allows for preparation or processing of the at least one electrolytic surface at a temperature of at least 600° C.

10. The apparatus of claim 7 wherein the high-temperature material allows for preparation or processing of the at least one electrolytic surface at a temperature of at least 1000° C.

11. The apparatus of claim 7 wherein the high-temperature material allows for preparation or processing of the at least one electrolytic surface at a temperature of at least 2000° C.

12. An apparatus for evaluating an electrochemical reaction, the apparatus comprising:
   an electrochemical cell comprising a cavity for containing a liquidus electrolyte, a first working electrode having at least one electrolytic surface at least partially within the cavity, and a counter electrode having at least one electrolytic surface at least partially within the cavity, the first working electrode comprising a body formed from aluminum and an external anodize coating and an insert supported by the body, each of the insert and the body consisting essentially of a high-temperature material allowing for preparation or processing of the at least one electrolytic surface at a temperature of at least 300 ° C.; and
   a drive system detachably coupled to the first working electrode or a portion thereof for effecting relative motion between the at least one electrolytic surface of the working electrode and a bulk portion of the liquidus electrolyte.

13. The apparatus of claim 12 wherein the drive system coupling to the first working electrode includes two independent electrical contact points.

14. The apparatus of claim 13 wherein one contact point is configured to carry current and the other contact point is configured for voltage sensing.

15. An apparatus for evaluating an electrochemical reaction, the apparatus comprising:
   an electrochemical cell comprising a cavity for containing a liquidus electrolyte, a first working electrode having at least one electrolytic surface at least partially within the cavity, and a counter electrode having at least one electrolytic surface at least partially within the cavity, the first working electrode comprising a body formed from steel and an insert supported by the body, each of the insert and the body consisting essentially of a high-temperature material allowing for preparation or processing of the at least one electrolytic surface at a temperature of at least 300° C.; and
   a drive system detachably coupled to the first working electrode or a portion thereof for effecting relative motion between the at least one electrolytic surface of the working electrode and a bulk portion of the liquidus electrolyte.

16. An apparatus for simultaneously evaluating multiple electrochemical reactions, the apparatus comprising:
a plurality of electrochemical cells, each of said plurality of electrochemical cells comprising a cavity for containing a liquidus electrolyte, a first working electrode having at least one electrolytic surface at least partially within the cavity, and a counter electrode having at least one electrolytic surface at least partially within the cavity; and
a drive system mechanically coupled by a common drive shaft to the first working electrode or a portion thereof of each of the plurality of electrochemical cells for simultaneously effecting relative motion between the at least one electrolytic surface of each working electrode and a bulk portion of its respective liquidus electrolyte.

17. The apparatus of claim 16 wherein the at least one electrolytic surface is defined by different materials as compared between each of said plurality of electrochemical cells.

18. The apparatus of claim 16 wherein the first working electrode comprises an electrically insulating body and an electrically conductive insert supported by the body.

19. The apparatus of claim 18 wherein said at least one electrolytic surface is formed on the insert.

20. The apparatus of claim 18 wherein the insert comprises a high-temperature material allowing for preparation or processing of said at least one electrolytic surface at a temperature of at least 300° C.

21. The apparatus of claim 16 wherein each of said plurality of electrochemical cells is movable independent from the other cells to vary an insertion depth of the at least one electrolytic surface relative to a depth of the liquidus electrolyte.

22. The apparatus of claim 16 wherein the first working electrode is a rotating disk electrode.

23. The apparatus of claim 16 further comprising a processor configured for controlling electrochemical reactions within each of said plurality of electrochemical cells.

24. The apparatus of claim 16 further comprising a processor configured for evaluating electrochemical reactions within each of said plurality of electrochemical cells.

25. The apparatus of claim 16 wherein the first working electrode is formed at least partially from a high-temperature material allowing for testing at a temperature of at least 80° C.

26. An apparatus for simultaneously evaluating multiple electrochemical reactions, the apparatus comprising an electrochemical cell comprising:
a cavity for containing a liquidus electrolyte;
a plurality of working electrodes each having at least one electrolytic surface positioned at least partially within the cavity, said at least one electrolytic surface being defined by different materials as compared between each of said plurality of working electrodes;
at least one counter electrode having at least one electrolytic surface positioned at least partially within the cavity; and
a drive system coupled to the first working electrodes or a portion thereof for effecting relative motion between said at least one electrolytic surface of the working electrode and a bulk portion of the liquidus electrolyte.

27. The apparatus of claim 26 wherein each of said plurality of working electrodes comprises an electrically insulating body and an electrically conductive insert supported by the body.

28. The apparatus of claim 27 wherein said at least one electrolytic surface is formed on the insert.

29. The apparatus of claim 27 wherein the insert comprises a high-temperature material allowing for preparation or processing of said at least one electrolytic surface at a temperature of at least 300° C.

30. A parallel electrochemical apparatus for screening a plurality of materials, the apparatus comprising:
a plurality of electrochemical cells, each of said plurality of electrochemical cells comprising a cavity for containing a liquidus electrolyte; and
a plurality of electrodes, each of said plurality of electrodes comprising at least one electrolytic surface for positioning at least partially within the cavity;
wherein each of the plurality of electrochemical cells is movable independent from the other cells to vary an insertion depth of the electrode within the cavity and the position of each of the plurality of electrochemical cells is controlled by a processor.

31. The apparatus of claim 30 wherein the electrode comprises a body and an insert supported by the body, said at least one electrolytic surface being formed on or integral with the insert.

32. The apparatus of claim 31 wherein each of the body and the insert comprises a high-temperature material allowing for processing of the at least one electrolytic surface at a temperature of at least 300° C.

33. The apparatus of claim 30 wherein the electrodes are rotating disk electrodes.

34. A method of making a working electrode, the method comprising:
providing a body;
applying an external coating to the body to create an external sleeve using a chemical process; and
inserting an insert formed from an electrode material into an opening in one end of the body;
wherein the material of the body and the material of the insert allow for preparation or processing of the working electrode at temperatures greater than 300° C.

35. The method of claim 34 wherein the external sleeve is formed from an electrical insulating material.

36. The method of claim 34 wherein the external sleeve is formed from an electrochemically inert material.

37. The method of claim 34 further comprising inserting the rotating disk electrode into an electrochemical cell for electrochemical screening.

38. The method of claim 34 wherein said chemical process comprises subjecting the body to chemical vapor deposition.

39. The method of claim 34 wherein said chemical process comprises growing a boron nitride layer to form the external sleeve.

40. The method of claim 34 wherein the body is formed from graphite.

41. The method of claim 40 wherein the insert is formed from carbon.

42. The method of claim 34 wherein said chemical process comprises anodizing external surfaces of the body.

43. The method of claim 42 wherein the body is formed from aluminum.

44. The method of claim 34 wherein the body is formed from steel.

45. The method of claim 44 wherein said chemical process comprises applying Silcosteel®.

46. The method of claim 34 wherein the materials of the body and the insert allow for processing or preparation of the rotating disk electrode at a temperature of at least 600° C.

47. The method of claim 34 wherein the materials of the body and insert allow for processing or preparation of the rotating disk electrode at a temperature of at least 2000° C.

48. The method of claim 34 further comprising detachably coupling the rotating disk electrode to a drive shaft.

49. A rotating disk electrode comprising:
an insert formed from an electrode material;
a tubular member having an opening formed at one end thereof for receiving the insert;
a coating applied to an external surface of the tubular member to form an electrical insulating sleeve; and
a physical vapor deposition coating applied to an exposed end of the insert to form an electrolytic surface;
wherein the material of the tubular member and the material of the insert allow for processing or preparation of the rotating disk electrode at temperatures greater than 300° C.

50. The rotating disk electrode of claim 49 wherein the coating applied to the external surface of the tubular member comprises boron nitride.

51. The rotating disk electrode of claim 49 wherein the materials of the tubular member and insert allow for processing of the rotating disk electrode at a temperature of at least 2000° C.

52. The rotating disk electrode of claim 49 wherein the sleeve has a thickness of about 0.1 mm to 1.0 mm.

53. The rotating disk electrode of claim 49 wherein the sleeve has a thickness of about 0.5 um to 50.0 um.

54. A rotating disk electrode comprising:
an insert formed from an electrode material;
a tubular member having an opening formed at one end thereof for receiving the insert;
an anodize coating applied to an external surface of the tubular member to form an electrical insulating sleeve; and
wherein the material of the electrical insulating sleeve and the material of the insert allow for processing or preparation of the rotating disk electrode at temperatures greater than 300° C.

55. The rotating disk electrode of claim 54 wherein the tubular member is formed from aluminum.

56. The rotating disk electrode of claim 54 further comprising a drive shaft assembly detachably coupled to the rotating disk electrode.

57. The rotating disk electrode of claim 56 wherein the drive shaft assembly is coupled to the rotating disk electrode with a slip fit.

58. The rotating disk electrode of claim 56 wherein the drive shaft assembly and rotating disk electrode comprise two separate electrical contact points when coupled together.

59. The rotating disk electrode of claim 58 wherein one contact point is configured to carry current and the other contact point is configured for voltage sensing.

60. A rotating disk electrode comprising:
an insert formed from an electrode material;
a tubular member formed from steel and having an opening formed at one end thereof for receiving the insert;
a coating applied to an external surface of the tubular member to form an electrical insulating sleeve; and
wherein the material of the electrical insulating sleeve and the material of the insert allow for processing or preparation of the rotating disk electrode at temperatures greater than 300° C.

61. The rotating disk electrode of claim 60 wherein the insert and the tubular member opening are sized to create a liquid tight seal therebetween.

62. A rotating disk electrode comprising:
an insert formed from an electrode material;
a tubular member having an opening formed at one end thereof for receiving the insert, wherein the thermal expansion coefficient of the tubular member is about ten times greater than the thermal expansion coefficient of the insert;
a coating applied to an external surface of the tubular member to form an electrical insulating sleeve; and
wherein the material of the electrical insulating sleeve and the material of the insert allow for processing or preparation of the rotating disk electrode at temperatures greater than 300° C.

63. A rotating disk electrode comprising:
an insert formed from an electrode material;
a tubular member having an opening formed at one end thereof for receiving the insert, wherein the thermal expansion coefficient of the tubular member is generally the same as the thermal expansion coefficient of the insert;
a coating applied to an external surface of the tubular member to form an electrical insulating sleeve; and
wherein the material of the electrical insulating sleeve and the material of the insert allow for processing or preparation of the rotating disk electrode at temperatures greater than 300° C.

64. A rotating disk electrode comprising:
a body formed from an electrical insulating material;
an insert formed from glassy carbon, supported by the body and comprising an electrolytic surface being formed on or integral with the insert;
wherein the material of the body and the material of the insert allow for processing or preparation of the electrolytic surface at a temperature of at least 300° C.

65. The rotating disk electrode of claim 64 wherein the body is formed from a ceramic material.

66. A rotating disk electrode comprising:
a body formed from sapphire;
an insert supported by the body and comprising an electrolytic surface being formed on or integral with the insert;
wherein the material of the body and the material of the insert allow for processing or preparation of the electrolytic surface at a temperature of at least 300° C.

67. The rotating disk electrode of claim 66 wherein the materials of the body and insert allow for processing of the rotating disk electrode at a temperature of at least 1000° C.

68. A method of making a working electrode, the method comprising:
providing a body;
applying an external coating to the body to create an external sleeve;
inserting an insert formed from an electrode material into an opening in one end of the body; and
performing a process on an exposed end of the insert to form the electrolytic surface, the electrolytic surface having a different composition than the insert;
wherein the material of the body and the material of the insert allow for preparation or processing of the working electrode at temperatures greater than 300° C.

69. The method of claim 68 wherein performing said process comprises applying a physical vapor deposition coating to said exposed end of the insert to form the electrolytic surface.

70. The method of claim 68 wherein performing said process comprises electroplating said exposed end of the insert to form the electrolytic surface.

71. The method of claim 68 wherein performing said process comprises modifying said exposed end of the insert by liquid dispensing a chemical solution.

72. The method of claim 68 wherein performing said process comprises modifying said exposed end of the insert with powder impregnation.

* * * * *